United States Patent

Lizzi

[11] Patent Number: 6,039,689
[45] Date of Patent: Mar. 21, 2000

[54] STRIPE ELECTRODE TRANSDUCER FOR USE WITH THERAPEUTIC ULTRASONIC RADIATION TREATMENT

[75] Inventor: Frederic Lizzi, Tenafly, N.J.

[73] Assignee: Riverside Research Institute, New York, N.Y.

[21] Appl. No.: 09/038,632

[22] Filed: Mar. 11, 1998

[51] Int. Cl.$^7$ ........................................ A61B 8/00
[52] U.S. Cl. .................... 600/439; 601/2; 601/3
[58] Field of Search ..................... 600/439, 458, 600/443, 447; 601/2–4; 73/67.85

[56] References Cited

U.S. PATENT DOCUMENTS

| | | | |
|---|---|---|---|
| 3,805,596 | 4/1974 | Kkahr | 73/678 S |
| 4,889,122 | 12/1989 | Watmough et al. | 600/439 |
| 5,143,074 | 9/1992 | Dory | 601/2 |
| 5,193,527 | 3/1993 | Schafer | 01/2 |
| 5,665,054 | 9/1997 | Dory | 600/439 |
| 5,873,845 | 2/1999 | Cline et al. | 601/3 |

OTHER PUBLICATIONS

Technical Program & Abstracts, 1996 IEEE *Ultrasonics Symposium Short Courses*, Nov. 3–6, 1996.

Mode scanning: heating pattern synthesis with ultrasound phased arrays, R.J. McGough, H. Wang, E.S. Ebbini and C.A. Cain, *Int. J. Hyperthermia, 1994*, vol. 10, No. 3, pp. 433–442.

Concentric–Ring and Sector–Vortex Phased–Array Applicators for Ultrasound Hyperthermia, Charles A. Cain, IEEE, and Shin–Ichiro Umemura, *IEEE Transactions on Microwave Theory and Technologies*, vol. M11–34, Ni. 5, May 1986.

*Primary Examiner*—William E. Kamm
*Assistant Examiner*—Ali M. Imam
*Attorney, Agent, or Firm*—Baker & Botts L.L.P.

[57] ABSTRACT

A spherical cap transducer is provided with at least one electrode formed as segments. The segments are selectively driven to provide asymmetrical ovoid effective radiation patterns for treatment of tissue with ultrasonic radiation.

10 Claims, 8 Drawing Sheets

STRIPE ELECTRODE TRANSDUCER FOR USE WITH THERAPEUTIC ULTRASONIC RADIATION TREATMENT

This invention was made in the performance of NIH Grant RO1-EY10369 awarded by the National Eye Institute of The National Institutes of Health.

BACKGROUND OF INVENTION

The present invention relates to therapeutic ultrasonic transducers and particularly to arrangements for controlling the effective beam width of therapeutic ultrasonic radiation and avoiding cavitation and other effects arising out of excess energy in a portion of the tissue being treated. In particular, the invention has application in treatment of ocular diseases, including glaucoma, retinal detachment and tumors.

It has been previously known to provide therapeutic ultrasonic radiation by use of a spherical cap transducer. This transducer provides a symmetrical focused beam with a circular cross-section at the focal plane. Such beams can provide thermally induced lesions with circular cross-sections, but are not optimum for treatment of tumors because the narrow circular beam requires a large number of exposures to treat the entire tumor region.

Another problem associated with a narrow circular beam is that production of broader therapeutic lesions can require excess energy intensity at or near the focal point, which can lead to cavitation, vaporization or tissue degassing, creating gas bodies that block ultrasound transmission to deeper tissue regions.

A prior approach has been described which uses annular transducer segments to control and adjust focusing of the transducer beam. This approach does not effectively spread the energy in one dimension only and can lead to off focal plane "hot" spots that can cause cavitation etc.

Another prior approach has been to use a planar phased array of transducer elements. Still another approach uses annular sectors on a spherical shell transducer. These approaches are complex and require provision of complex radio frequency (RF) amplitude and phase control circuits.

It is an object of the invention to provide an improved therapeutic ultrasound transducer with a beam having a broad pattern in one direction and a narrow pattern in another transverse direction to provide easier and more effective therapeutic treatment with high intensity focused ultrasound.

It is a further object to provide a transducer that avoids high intensity regions that can cause cavitation, vaporization or tissue degassing effects.

SUMMARY OF THE INVENTION

In accordance with the present invention there is provided apparatus for radiating therapeutic ultrasonic radiation for treatment of tissue. The apparatus includes a transducer in the shape of a partial sphere formed of piezoelectric material having first and second radially separated surfaces and conductive electrodes on the surfaces. One of the electrodes is segmented into electrode segments including segments arranged on opposite sides of a central plane. A circuit is provided for selectively providing electrical signals to the electrodes to cause the transducer to provide ultrasonic radiation patterns at a focal plane of the transducer which provide a narrow beam width of thermal effect in the central plane and a broad beam width of thermal effect on a perpendicular plane.

Preferably the segments are electrode strips separated along planes parallel to the central plane. The circuit can alternately energize only a central strip, only the outer strips or a combination of the strips to provide sonic radiation patterns having a single broad lobe in the perpendicular plane or multiple narrow lobes in the perpendicular plane.

For a better understanding of the present invention, together with other and further objects, reference is made to the following description, taken in conjunction with the accompanying drawings and its scope will be pointed out in the appended claims.

DESCRIPTION OF THE PREFERRED EMBODIMENT

Figure 1:
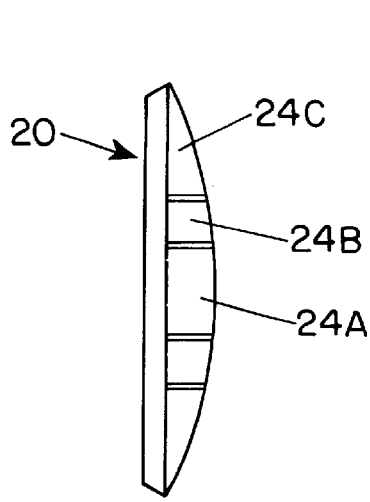
FIG. 1 is a side view of an ultrasonic therapeutic transducer in accordance with the present invention.
Figure 2:
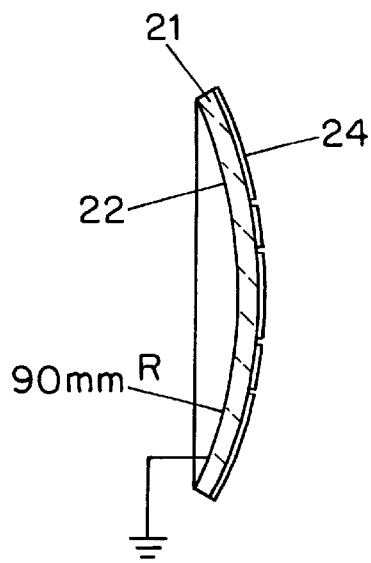
FIG. 2 is a cross-sectional view of the FIG. 1 transducer.
Figure 3:
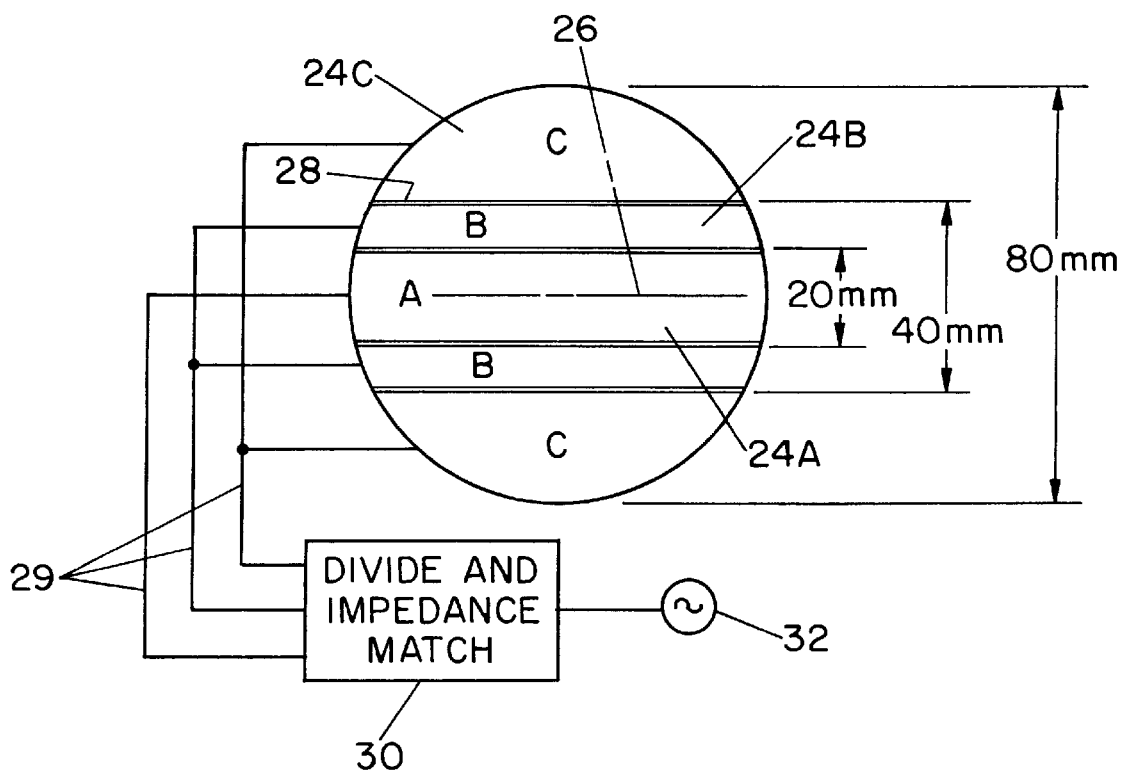
FIG. 3 is a rear view of the FIG. 1 transducer showing connections to driving circuits.

Referring to FIGS. 1 to 3 there is shown a therapeutic ultrasound transducer 20 in accordance with a preferred embodiment of the present invention. Transducer 20 is a spherical cap transducer of a type known in the art. The transducer includes a spherical shell segment of piezoelectric material, such as PZT4, with a spherical radius of 90 mm and a segment radius of 80 mm. The shell thickness is selected to have a resonance, such as the third harmonic resonance at the frequency to be transmitted. For example, for a transmission frequency of 4.7 MHZ, using the third harmonic, the shell thickness is about 1 mm. The transducer material and thickness can also be selected to provide operation within a finite bandwidth of frequencies. Transducer 20 includes an inner electrode 22 and an outer electrode 24, each comprising a metal coating on the transducer inner and outer surfaces. As is known in the art, by supplying radio frequency electrical signals between electrodes 22 and 24, transducer 20 is caused to emit ultrasonic waves into the surrounding media. Typically a conical coupling chamber, filled with degassed water, is provided on the side of transducer 20 corresponding to electrode 22, to provide an acoustically matched conduit for ultrasonic radiation toward the spherical center, whereat the ultrasonic waves converge to a narrow circular focal point of high intensity.

Such focusing spherical cap transducers have been used to provide ultrasonic therapeutic radiation, for example, for non-invasive treatment of the above noted conditions of the eye using high-intensity pulses with durations near 5 sec.

While transducers of the type shown in FIGS. 1 to 3 usually are provided with continuous electrodes 22 and 24, in transducer 20, electrode 24 is divided into five symmetrically arranged segments labeled 24A, 24B, 24C in FIG. 3. The segments are divided by insulating, i.e. unplated, gaps 28 having a width of 1 mm. In practice, electrode 24 can be formed as a continuous plating and gaps 28 can be formed by sandblasting the plating away along each strip.

Those familiar with the art will recognize that electrode 22 can alternately or additionally be divided into electrode segments, but since the segments require attachment of driving leads, it is more convenient to provide a continuous inner electrode 22, which may be grounded, and provide segments on the spherically outer electrode 24.

Segments 24A, 24B, 24C are divided by gaps that lie in parallel planes. It will be recognized, however, that there is no particular requirement for such parallel relationship, except for convenience of fabrication, e.g. the strip plating can be removed by a stationary tool as the transducer is rotated about a spherical axis, perpendicular to central plane 26 of transducer 20.

FIG. 3 shows leads 29 interconnecting transducer electrode segment strips 24A, 24B and 24C in symmetrical pairs to signal divider and impedance matching circuit 30, which receives RF driving signals from pulsed oscillator 32. According to the present invention, desired shaping of the ultrasonic radiation beam in the focal plane is achieved by supplying driving signals from divider circuit 30 to one or more of the segments of electrode 24. Accordingly, only one or more connecting wires 29 need be provided, and indeed, unused electrode segments need not be present.

The driving of the electrode segments is selected to provide a shaping of the ultrasonic energy beam at the focal plane which provides therapeutic treatment to a region in a desired geometric pattern. Typically for treating small areas, the desired pattern may be a small circular area of the focal plane. This is achieved by known transducers having continuous electrodes on the inner and outer spherical surfaces.

In other treatments, however, wherein it is desired to treat a larger area, an ovoid pattern of effective radiation in the focal plane may be desired, whereby the surgeon can irradiate one portion of the region to be treated with a pattern that is wide in one plane and narrow in a perpendicular plane. This treatment pattern can be incrementally stepped along the region to be treated in the direction of the perpendicular plane until the entire region has been irradiated. If necessary a second or third row in the plane of the broad radiation pattern can be used, but the need for a grid of narrow beam rows, as required by the prior art, can be avoided.

To achieve the effective treatment of an ovoid region, it is first possible to alter the actual ultrasonic radiation beam by spreading the pattern by driving only the central segment 24A of transducer electrode 24. Accordingly, divide and impedance match circuit 30 would need to provide only an impedance matching of oscillator 32 to electrode segment 24A, and need not provide a dividing function. Indeed, if only a single pattern is desired, segments 24B and 24C need not be present.

Figure 5:
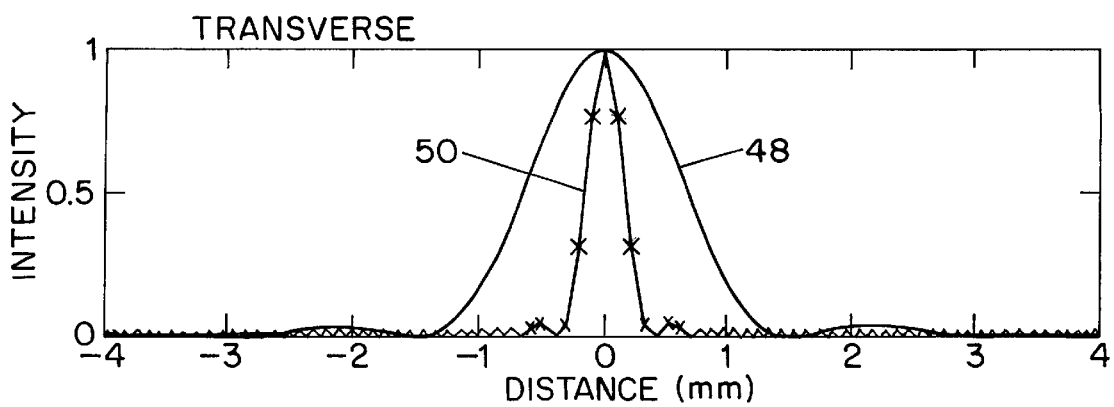
FIG. 5 is a graph depicting the transverse focal plane patterns of the FIG. 1 transducer using a first driving arrangement.
Figure 6:
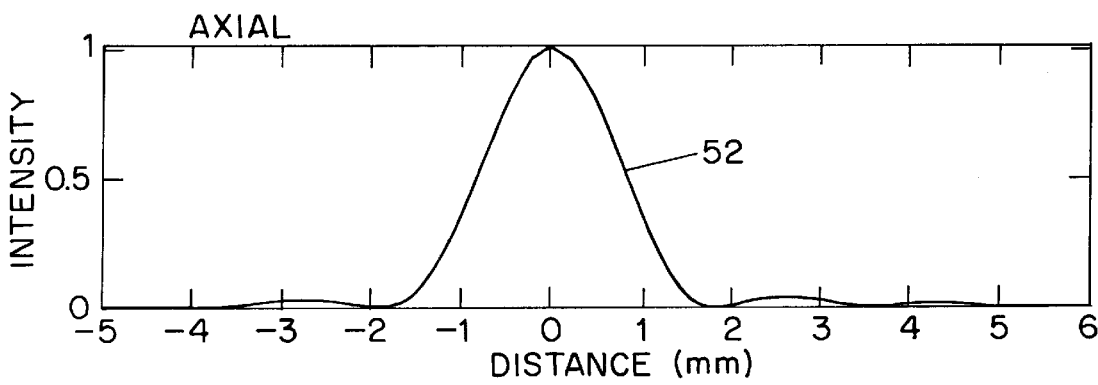
FIG. 6 is a graph depicting the axial intensity of the ultrasonic radiation of the FIG. 1 transducer in the focal plane region.

FIG. 5 shows the focal plane pattern that results from this first arrangement, driving segment 24A only, as relative intensity against distance from the central axis of plane 26. Graph 48 shows the pattern in the plane transverse to plane 26. Graph 50 shows the pattern in plane 26. Since segment 24A has a substantially narrower effective aperture width in the perpendicular plane, the pattern is much broader in that plane. FIG. 6 shows intensity along the central axis in the region of the focal plane, with maximum intensity near the focal point, indicated as zero on the graph's abscissa.

Using the first segment driving arrangement, the shape of the treatment region becomes ovoid in the focal plane, but is not sharply defined since the radiation intensity on either side of curve 48 falls off at a more gradual slope.

It will be recognized that a multimode transducer may be provided by driving segment 24A by itself to provide a first ovoid beam shape, or alternatively driving all segments to provide a circular beam shape. An intermediate ovoid beam can also be provided by driving segments 24A and 24B.

Shaping of the ultrasonic beam pattern to achieve an ovoid treatment region can also be achieved using additional electrode segment driving arrangements that take into consideration the thermal characteristics of the tissue being treated. Such alternate arrangements are arrived at using the recognition that it is not the ultrasonic energy that modifies tissue but the temperature rise that results from dissipation of ultrasonic energy that modifies tissue. Since thermal energy is conducted over distances in tissue, the effective tissue treatment region can be different from the radiation profile of the ultrasonic beam. Further, the temperature rise caused in nearby tissue is a function of the irradiation time, since there is an inherent time lag in thermal diffusion.

Figure 7:
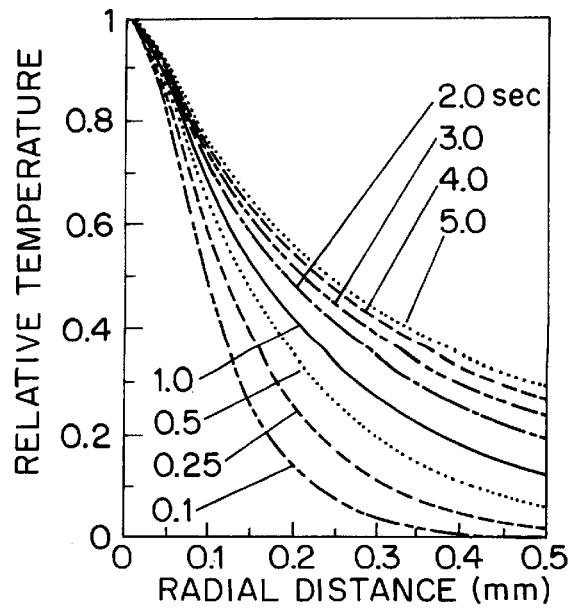
FIG. 7 is a graph showing normalized thermal energy dispersion as a function of radiation time interval.

FIG. 7 is a graph showing the normalized temperature rise in tissue as a result of heating by an infinitely long line source of heat, for varying heating time durations. The graph shows that the rate of temperature fall-off with radial distance decreases for increased heating time duration.

Giving consideration to thermal diffusion effects, it becomes possible to provide a transducer driving arrangement wherein the energy is distributed in multiple ultrasonic pattern lobes, to reduce peak energy density. This can be achieved by driving segments 24C only.

Figure 8:
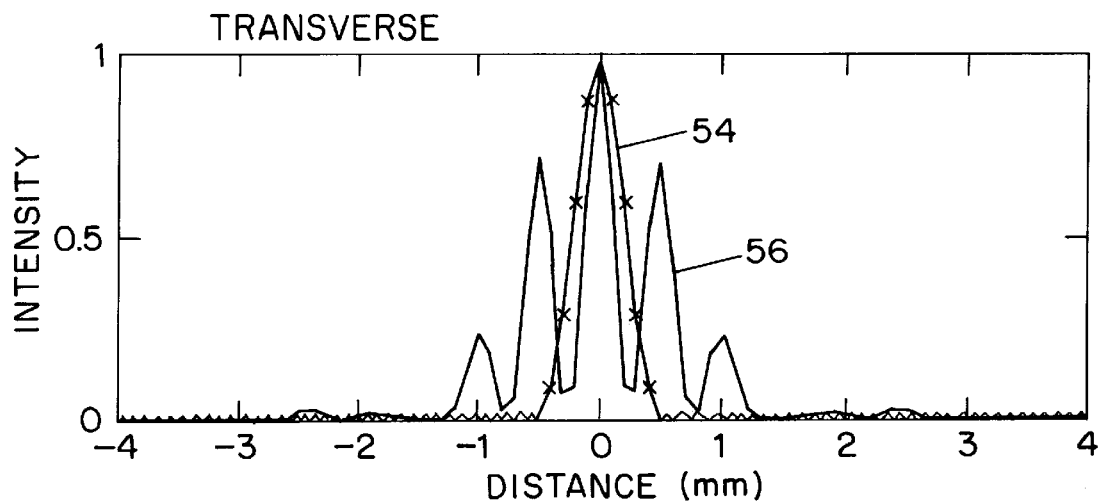
FIG. 8 is a graph depicting the transverse focal plane patterns of the FIG. 1 transducer using a first alternate driving arrangement.
Figure 9:
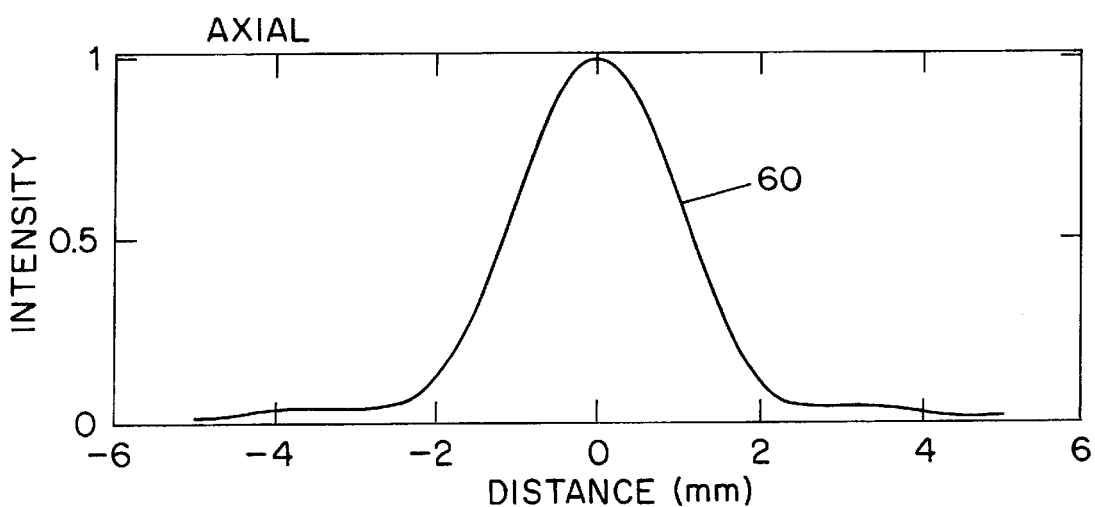
FIG. 9 is a graph depicting the axial intensity of the ultrasonic radiation of the FIG. 1 transducer using a first alternate driving arrangement.
Figure 10:
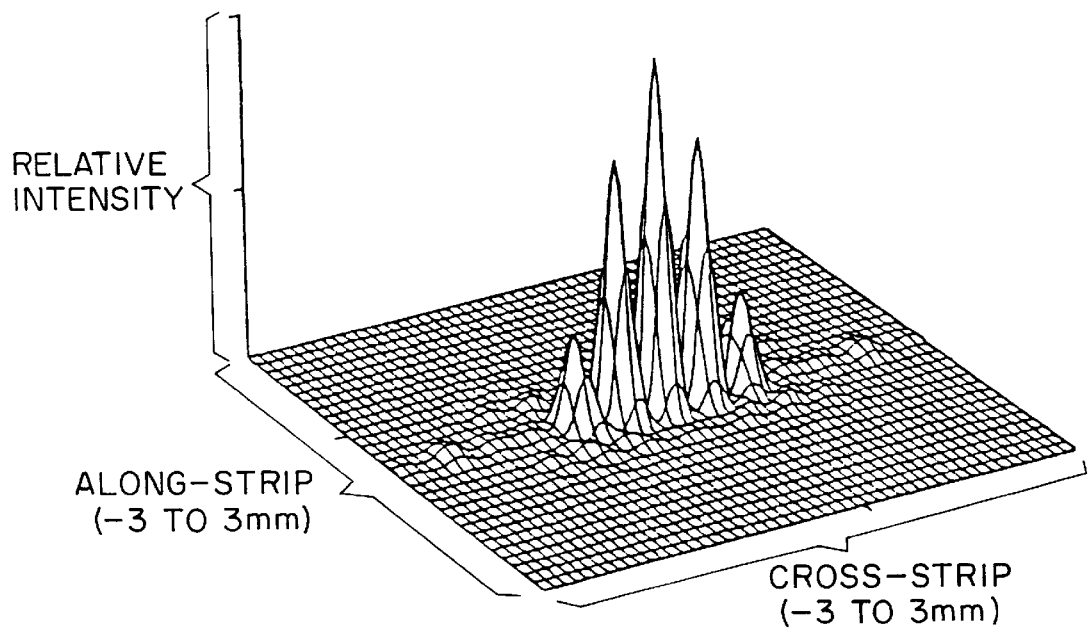
FIG. 10 is an intensity pattern of the FIG. 1 transducer using a first alternate driving arrangement.

FIG. 8 shows the resulting focal plane patterns in central plane 26 as curve 54, and in the perpendicular plane as curve 56. Curve 56 has three high intensity central lobes, providing an effective broad pattern with high rate of intensity fall off. The spacing between lobes is inversely proportional to the distance between the strips and to frequency. For a specified spacing, the number of significant lobes is inversely proportional to the width of each strip and to frequency. The axial pattern curve 60 shown in FIG. 9 is similar to the first driving arrangement shown in FIG. 6. Relative intensity values in the focal plane are shown in FIG. 10.

Figure 4:
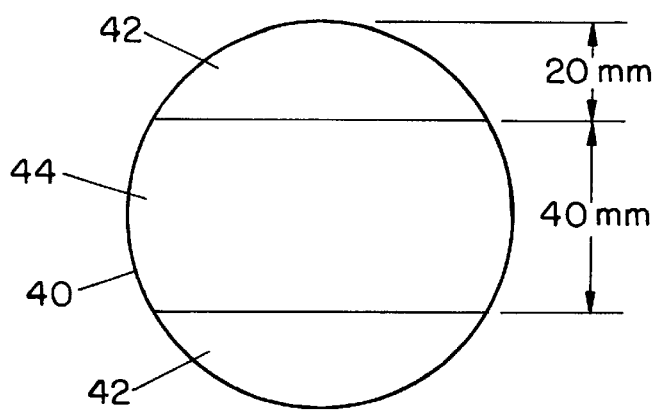
FIG. 4 is a rear view of an alternate transducer in accordance with the invention.

The same pattern effect can be achieved with a transducer 40 having only the outer segments 42 with a wide gap 44, as shown in the rear view of FIG. 4.

Figure 12:
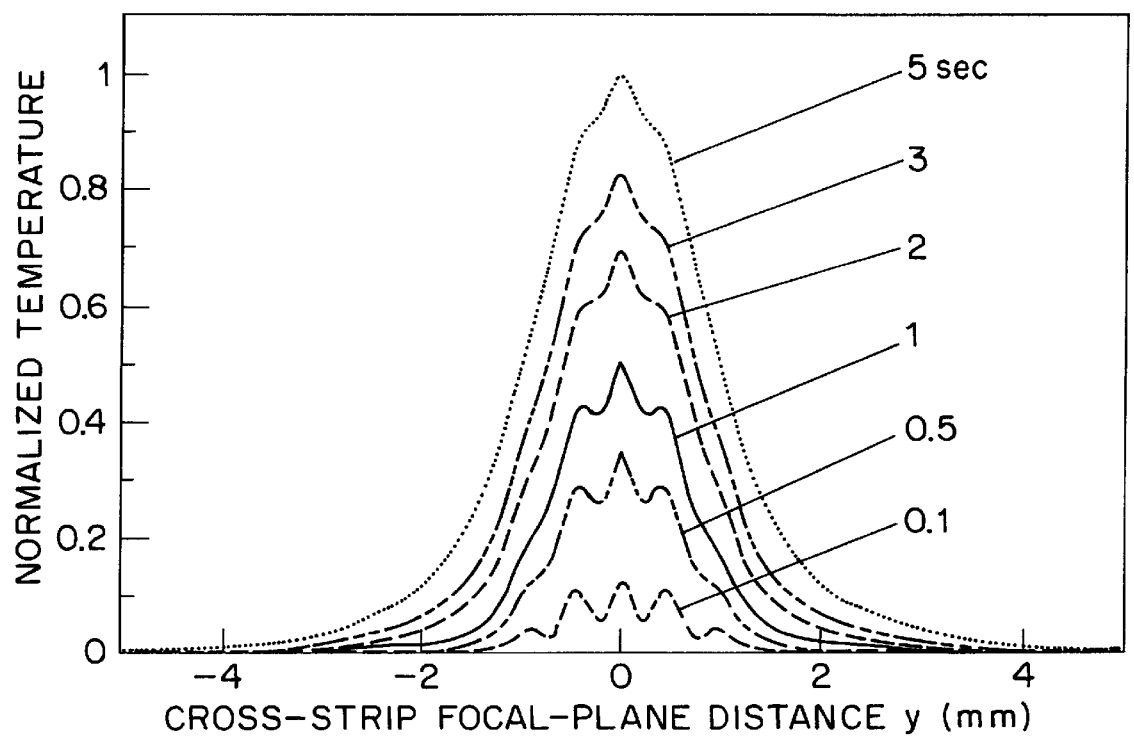
FIG. 12 is a graph illustrating temperature rise as a function of time for tissue at the focal plane of the FIG. 1 transducer using the first alternate driving arrangement.

The thermal diffusion effects fill in the nulls between the three main lobes of curve 56, according to the exposure time duration, resulting in tissue temperature effect patterns shown in FIG. 12. After about 0.5 seconds exposure, the tissue temperature effect pattern has a broad central lobe with steep sides, giving a well defined ovoid treatment area.

Figure 11:
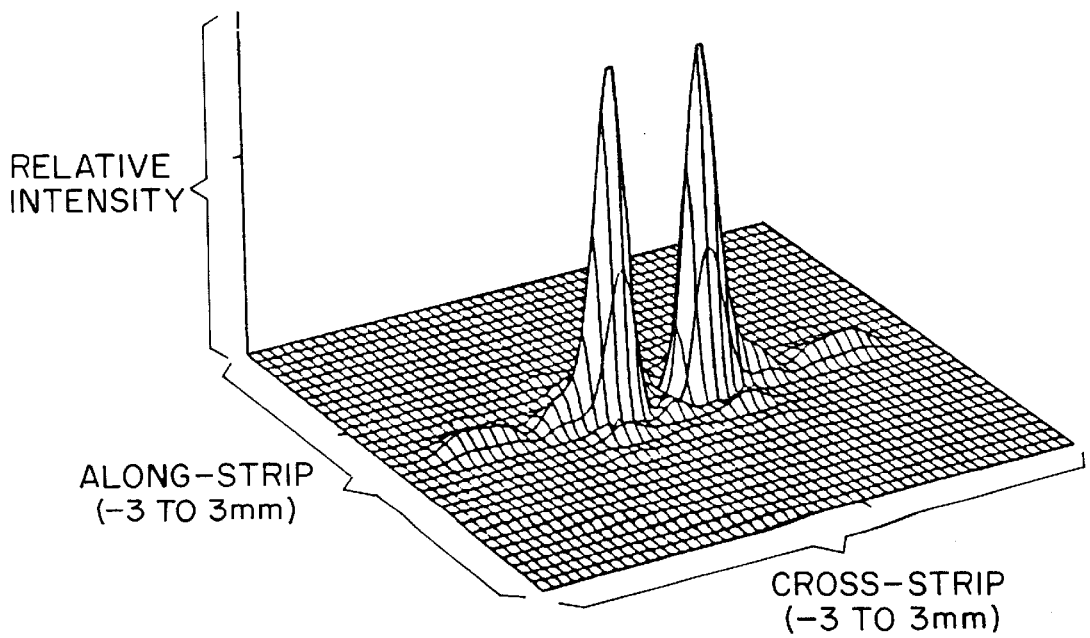
FIG. 11 is an intensity pattern of the FIG. 1 transducer using a second alternate driving arrangement.
Figure 13:
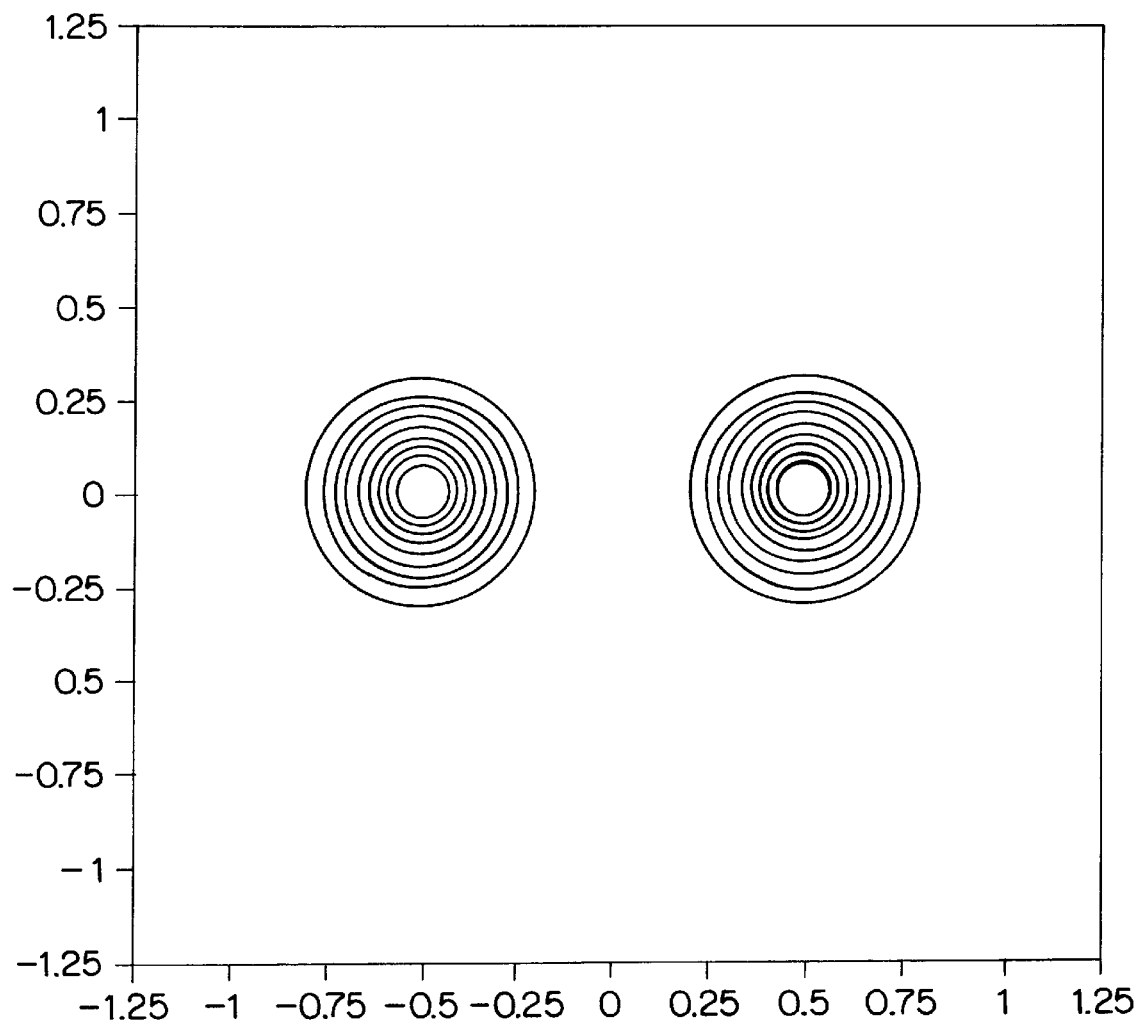
FIG. 13 is a graph showing estimated computed isotherm profiles for tissue at the focal plane of the FIG. 1 transducer using the second alternate driving arrangement for a 0.1 second irradiation.
Figure 14:
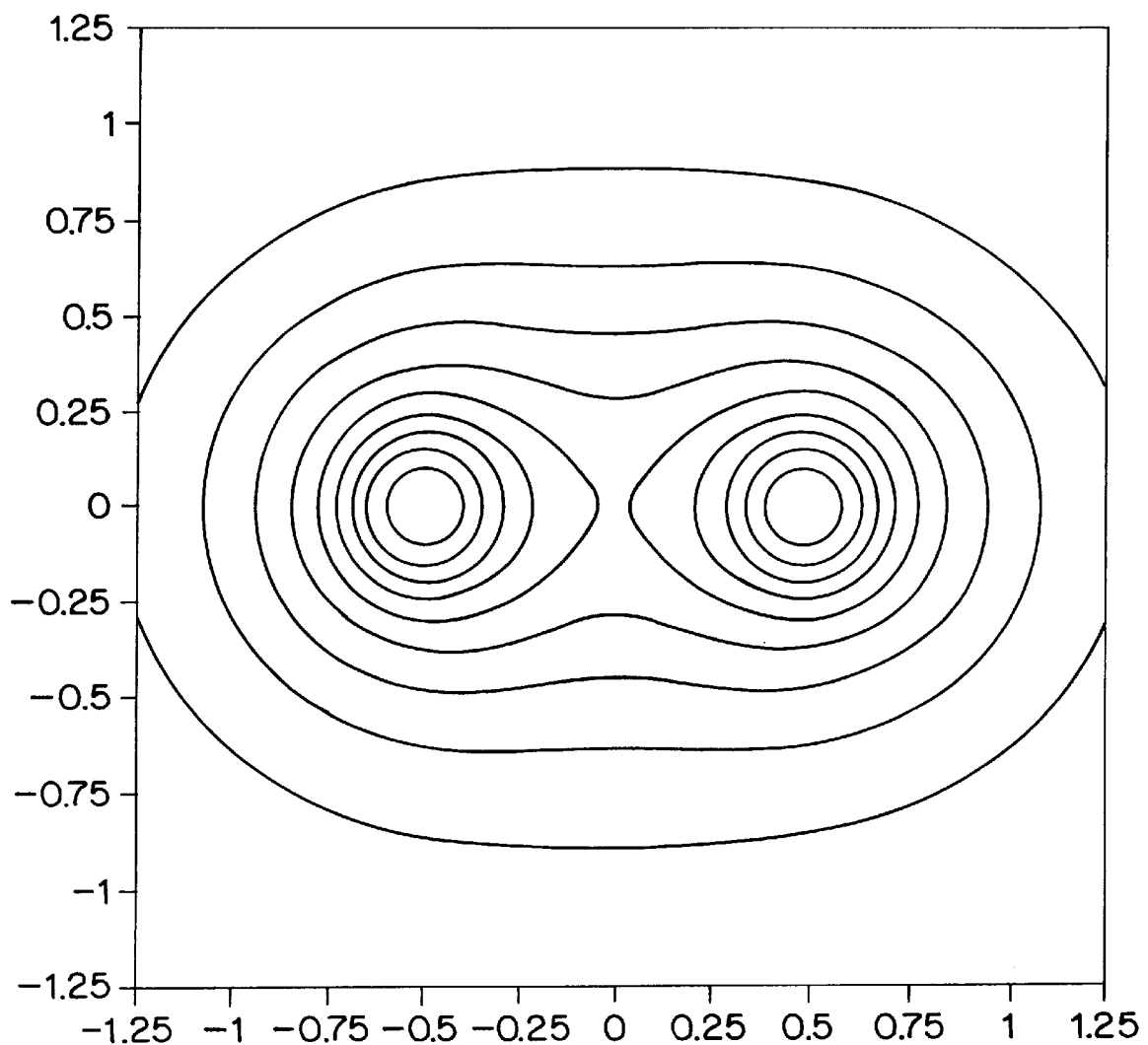
FIG. 14 is a graph showing estimated computed isotherm profiles for tissue at the focal plane of the FIG. 1 transducers using the second alternate driving arrangement for a 2.0 second irradiation.

A still further driving arrangement calls for driving segments with different voltage values and phase to achieve a two lobe radiation pattern in the focal plane shown as relative intensity values in FIG. 11. Segments 24A, 24B, and 24C are driven with relative driving voltages of −2, 1, and 1, respectively, to provide an on-axis null. Estimated thermal diffusion of the heating effect is illustrated as isothermal contours for a 0.1 second pulse duration in FIG. 13 and a 2.0 second duration in FIG. 14, resulting in the desired ovoid effective treatment pattern.

Desirable heating patterns may also be obtained by rapidly sequentially switching from one driving arrangement to another driving arrangement. Sequential driving arrangements can use different frequencies to control the location of intensity lobes. Several frequency components within the transducer's bandwidth may also be supplied simultaneously in a single driving arrangement to adjust composite heating patterns.

Figures 15, 16:
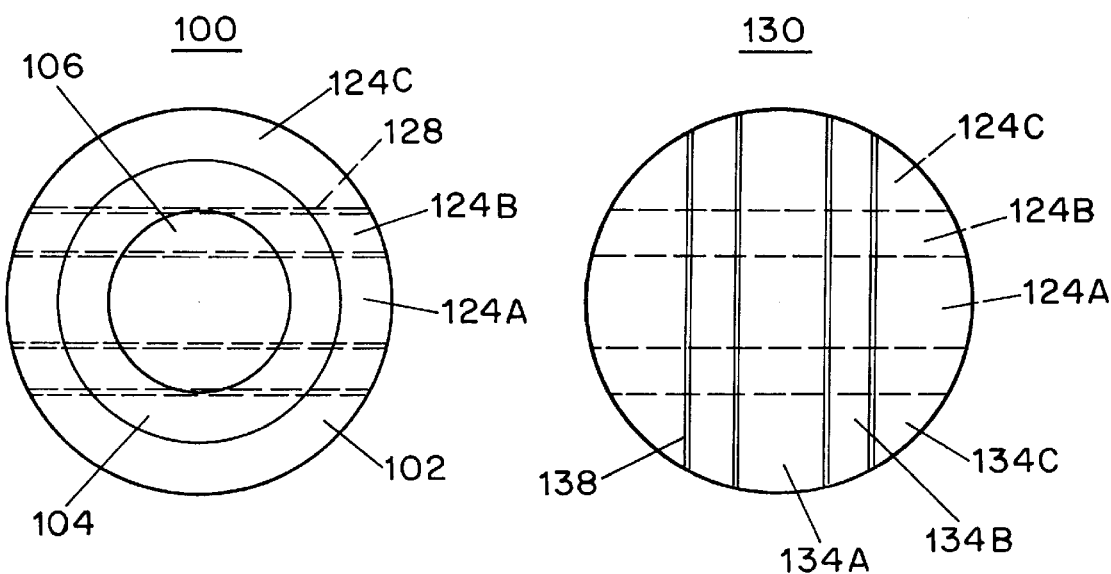
FIG. 15 is a rear view of a further alternate transducer in accordance with the invention.
FIG. 16 is a rear view of another alternate transducer in accordance with the invention.

FIG. 15 shows a rear view further alternate transducer 100 of the invention wherein the strip-shaped electrode segments 124A, 124B, 124C separated by gaps 128 formed on the inner spherical surface of the transducers. The outer spherical surface has an electrode formed as annular segments 102, 104 and 106. Applying known techniques, signals may be applied to electrode annular segments 102, 104 and 106 to adjust the focal length of the transducer in front of or behind the focal plane at the spherical apex. Segments 124A, 124B and 124C can be used to adjust the beam shape as described. Annular segments 102, 104, 106 are preferably on the outer spherical surface to avoid coupling wires in the radiation field. In addition, the phase of excitation signals delivered to the upper and lower sub-segments of segments 124C or 124B can be altered to steer the beam axis in the plane perpendicular to the strip edges.

FIG. 16 shows still another alternate embodiment wherein parallel strip electrode segments 124A, 124B and 124C are provided on the inner spherical surface, as in FIG. 15, while parallel strip segments 134A, 134B and 134C, separated by gaps 138 and perpendicular to segments 124A, 124B and 124C, are provided on the outer spherical surface.

The FIG. 16 arrangement can be used to adjust effective treatment beam width in two perpendicular directions using the described driving arrangements. Alternatively one set of parallel strips can be driven with phased signals to provide a scanning ultrasonic beam as described with respect to the FIG. 15 embodiment.

While there have been described what are believed to be the preferred embodiments of the present invention, those skilled in the art will recognize that other changes and modifications may be made thereto without departing from the spirit of the invention and it is intended to claim all such changes and modifications as fall within the true scope of the invention.

I claim:
1. Apparatus for providing therapeutic ultrasonic radiation for treatment of tissue, comprising:

a transducer in the shape of a partial sphere formed of piezoelectric material having first and second radially separated surfaces;

a conductive electrode on each of said surfaces, at least one of said electrodes being segmented into electrode segments said electrode segments including segments on opposite sides of a central plane;

and a circuit for selectively providing electrical signals to said electrodes to provide ultrasonic radiation patterns at a focal plane of said transducer which provide a narrow beam width of thermal effect in said central plane and a broad beam width of thermal effect in a plane which is perpendicular to said central plane.

2. Apparatus as specified in claim 1 wherein said electrode segments comprise electrode strips separated along planes substantially parallel to said central plane.

3. Apparatus as specified in claim 2 wherein said electrode strips comprise a central strip, a first pair of intermediate strips arranged on opposite sides of said central strip and a second pair of outer strips arranged on opposite sides of said intermediate and central strips.

4. Apparatus as specified in claim 3, wherein said circuit provides signals to said electrode strips with selected phase between at least some of said strips and with selected amplitude to reduce on axis ultrasonic energy at said focal plane.

5. Apparatus as specified in claim 1 wherein said circuit comprises an oscillator and circuits for coupling signals to selected ones of said electrode segments.

6. Apparatus as specified in claim 5 wherein said electrode segments comprise at least one inner electrode segment and at least one pair of outer electrode segments, and wherein said circuits provide said signals to said inner electrode.

7. Apparatus as specified in claim 5 wherein said electrode segments comprise at least one pair of outer electrode segments spaced apart from each other on opposite sides of said central pane, and wherein said circuits couple said signals to said pair of outer electrode segments.

8. Apparatus as specified in claim 1 wherein the other of said electrodes is segmented into annular segments, and wherein said circuit provides signals to said annular segments with selected phase to thereby adjust focusing of said ultrasonic radiation.

9. Apparatus as specified in claim 1 wherein the other of said electrodes is segmented into second electrode segments, including second electrode segments on opposite sides of a plane perpendicular to said central plane.

10. A multimode ultrasonic therapeutic apparatus comprising a transducer comprising a spherical segment of piezoelectric material, having inner and outer spherical surfaces, and first and second electrodes on said spherical surfaces, one of said electrodes comprising electrode segments, including segments on opposite sides of said spherical surface, and circuits for driving said electrode segments of said transducer in at least a first mode providing an ovoid effective radiation beam shape at the focal plane of said transducer and a second mode providing a substantially round effective radiation beam shape at the focal plane of said transducer.

* * * * *